(12) United States Patent
Bi

(10) Patent No.: US 10,845,285 B1
(45) Date of Patent: Nov. 24, 2020

(54) FAST RESPONSE FLUID PROPERTIES MONITORING SYSTEM

(71) Applicant: Hongfeng Bi, Houston, TX (US)

(72) Inventor: Hongfeng Bi, Houston, TX (US)

(73) Assignee: Hongfeng Bi, Houston, TX (US)

( * ) Notice: Subject to any disclaimer, the term of this patent is extended or adjusted under 35 U.S.C. 154(b) by 69 days.

(21) Appl. No.: 16/119,436

(22) Filed: Aug. 31, 2018

(51) Int. Cl.
*G01N 11/14* (2006.01)
*G01N 33/28* (2006.01)
*G01N 11/00* (2006.01)

(52) U.S. Cl.
CPC ......... *G01N 11/14* (2013.01); *G01N 33/2823* (2013.01); *G01N 2011/0026* (2013.01)

(58) Field of Classification Search
CPC ............... G01N 11/14; G01N 33/2823; G01N 2011/0026
See application file for complete search history.

(56) References Cited

U.S. PATENT DOCUMENTS

| | | |
|---|---|---|
| 4,557,142 A | 12/1985 | Hensley et al. |
| 8,392,121 B2 | 3/2013 | Zamora |
| 9,134,291 B2 | 9/2015 | Jamison et al. |
| 9,459,330 B2 * | 10/2016 | Freedman ............. G01R 33/30 |
| 9,568,408 B2 | 2/2017 | Jamison |
| 2016/0230482 A1 * | 8/2016 | Rapoport ............. G01N 24/081 |
| 2018/0172660 A1 * | 6/2018 | Miller ................ G01N 33/2823 |

* cited by examiner

*Primary Examiner* — Ryan D Walsh

(57) ABSTRACT

A fast response fluid monitoring system (300) used for fast evaluations and predictions of the properties of a drilling fluid or a fracturing fluid (204) onsite of an oilfield operation, by measuring the fluid properties under two shear rates at current temperature, predicting the fluid properties under other shear rates and under an elevated standard testing temperature, and comparing and updating results of the test to the predicted results to optimize next-time predicting practice.

13 Claims, 6 Drawing Sheets

FAST RESPONSE FLUID PROPERTIES MONITORING SYSTEM

CROSS-REFERENCE TO RELATED APPLICATIONS

Not applicable

BACKGROUND

Field of Invention

The present invention pertains to a method and apparatus for fast monitoring of a fluid, and more particularly, but not by way of limitation, a drilling fluid or fracturing fluid, onsite of an oilfield operation. Rheology characteristics, such as shear stress, shear rate, viscosity, etc., can be difficult to determine under down-hole conditions. This apparatus can be used to quickly evaluate and predict the properties of a drilling fluid, and a fracturing fluid based on initial measurements, and provides a strategy to adjust the fluid properties for a drilling or fracturing operation.

Description of Prior Art

Drilling fluids or mud are frequently used in oil and gas drilling operations. These fluids serve many purposes including, but not limited to, providing hydrostatic pressure to prevent formation fluids from entering the well bore, and keeping the drill bit cool and clean during drilling. Drilling fluids also serve the purpose of carrying out drill cuttings, suspending the drill cuttings while drilling is paused, and also when the drilling assembly is brought in and out the hole. The drilling fluids used for a particular job are selected to avoid formation damage and to limit corrosion. In the oil and gas industry certain personnel, such as a mud engineer, could be called upon to measure the current conditions of the drilling fluid properties. Some of the drilling fluid properties can be measured using a viscometer that can measure viscosity and gel strength. Two speeds of rotation, 300 rpm and 600 rpm, are available in most viscometers. In a popular torsion spring type viscometer its dial reading is proportional to the shear stress values. At 300 rpm, the dial reading (511 sec-1) is the same as a viscosity reading in centipoise. These shear stress readings are used to monitor the non-Newtonian properties of the drilling fluid. The Bingham plastic rheology model coefficients of plastic viscosity (PV) and yield point (YP) are calculated from the shear stress values measured at shear rates of 300 and 600 rpm. The PV and YP are calculated from the following equations, $$PV = \Theta_{600} - \Theta_{300}$$

$$YP = \Theta_{300} - PV$$

where PV is calculated in centipoise and $\Theta_{600}$ is the shear stress value measured at a shear rate of 600 rpm, YP is calculated in lb/100 ft$^2$ and $\Theta_{300}$ is the shear stress values measured at a shear rate of 300 rpm.

Along with PV and YP, shear stresses under other shear rates are needed to fully describe the property of the drilling fluid. These tested shear rates are potentially 3 rpm, 6 rpm, 100 rpm and 200 rpm. Additionally 10 seconds and 10 minutes gel strength measurement processes according to API 13 and API 10 are needed to measure gel strength of drilling fluid or drilling cement to fully describe the fluid properties. Normally it takes about 10 to 20 minutes to heat a drilling fluid from room temperature to 120° F. and it takes another 10 minutes or more to test 10 minutes gel strength.

Hydraulic fracturing has been used for over 60 years in over one million different wells. It is widely used in well stimulation for low-permeability formation, especially for when extracting natural gas from shale, tight stone, and coal beds. Hydraulic fracturing uses water pressure to create hairline fractures in rocks so natural gas or oil can flow through. Fracturing fluid systems are designed to implement a treatment per design to help increase production and improve the operator's return on investment. An optimized fluid system can result in minimized formation and fracture face damage, maximized overall results, as well as reduce the impact on drinking water and prevent other types of environmental damage.

U.S. Pat. No. 4,557,142 presents a method and apparatus for real time measuring of multiple properties of drilling fluids. It comprises of a pump for transferring fluid, suction and valves for connecting with the reservoir of drilling fluid to be measured, a weight and viscosity measuring device for measuring fluid properties, etc. However, this method for measuring drilling fluid properties, such as the ten-minute gel strength, requires some time to finish the measurement. This required time is not fast enough for the mud engineer to adjust the drilling fluid during the drilling operation.

U.S. Pat. No. 8,392,121 discloses a system for monitoring fluids at a drilling location. The system includes a viscometer that contains a heating cup and a pump. This system is capable of pumping a sample fluid into a heater cup to measure multiple properties of the sample fluid. The system also includes a cleaning fluid tank to clean the heating cup. This system doesn't provide a method of analyses or an estimate of the properties of the sample fluid without having to wait for heating or pre-conditioning of the fluid.

U.S. Pat. No. 9,134,291 discloses a system for analyzing multiple properties of drilling fluids. The system includes a pump and two reversible fluid ports with a means to transfer drilling fluid through a fluid analysis system. Although this system has many advantages, the system measurements take time to pre-condition the fluid, read the signal from sensors, and also it takes time for the mud engineer to interpret.

U.S. Pat. No. 9,568,408 presents a method for determining rheological quantities of a drilling fluid using apparent viscosity under extreme pressure and temperature conditions. The methods for scaling rheological quantities comprise of measuring an apparent viscosity of a drilling fluid at the first, second and third reference temperature and pressure conditions, determining a rate of change in apparent viscosity with respect to temperature or pressure, and scaling a rheological quantity between initial set and final set of pressure and temperature conditions by using the rate of change. The limitation of this method is that it is only valid for apparent viscosity. Viscosity is defined as the relationship between shear stress and shear rate. Apparent viscosity is the viscosity of the fluid at a specific shear rate. In a real drilling operation, the shear rate is a variable during the drilling operation; this is because drilling fluids are non-Newtonian, meaning that their viscosity is not constant for all shear rates and vice versa. Apparent viscosity also does not give a rheology profile. This can cause some difficulty when estimating the real viscosity under the real formation condition.

Viscosity and other rheological properties of a drilling fluid are normally measured and reported at standard temperatures. In order to accomplish this, the drilling fluid must be heated from its current temperature to 120° F. for most wells or 150° F. for high-temperature wells. Heating a drilling fluid to these elevated standard temperatures is time consuming; it may take 20 minutes or more for the drilling fluid to be at the desired temperature. Gel strengths refer to the shear stress required to initiate flow after static periods of time. These measurements such as the ten minute gel strength and the thirty minute gel strength are helpful to find shear stress at a low shear rate but are also time consuming in an industry that requires fast results. The benefit of the enclosed invention is that it provides a practical and affordable method for immediate and accurate predictions of the properties of a drilling fluid at a drilling location without compromising its integrity and performance. This invention also saves at least thirty minutes of time that would have been used to heat the drilling fluid and to wait for the gel strength measurement.

SUMMARY OF THE PRESENT INVENTION

The present invention pertains to a method and apparatus for fast evaluation and prediction of fluid properties of drilling fluids and fracturing fluids on the site of an oilfield operation. Rheology characteristic, such as shear stress, shear rate, viscosity, etc., can be difficult to quickly determine under down-hole or surface conditions. This apparatus can be used to measure the properties of drilling fluids and fracturing fluids under a defined shear rate or stirring rate. The apparatus also allows for fast predictions of the properties of drilling fluids and fracturing fluids based on initial measurements, and provides a strategy for adjusting the fluid properties for onsite operation.

OBJECTS AND ADVANTAGES

From the description above, a number of advantages of the fast response fluid properties monitoring system become evident:
a. to provide a method and an apparatus for promptly obtaining fluid properties used in fluid treatment programs for an onsite drilling or fracturing operation;
b. to provide a method of finding rheological properties of a drilling fluid quickly without a need to heat drilling fluid or collect lengthy gel strength measurements Further objects and advantages of the fast response fluid properties monitoring system will become apparent from a consideration of the drawings and ensuing descriptions.

DRAWING FIGURES

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and the benefit of this disclosure.

Figure 1:
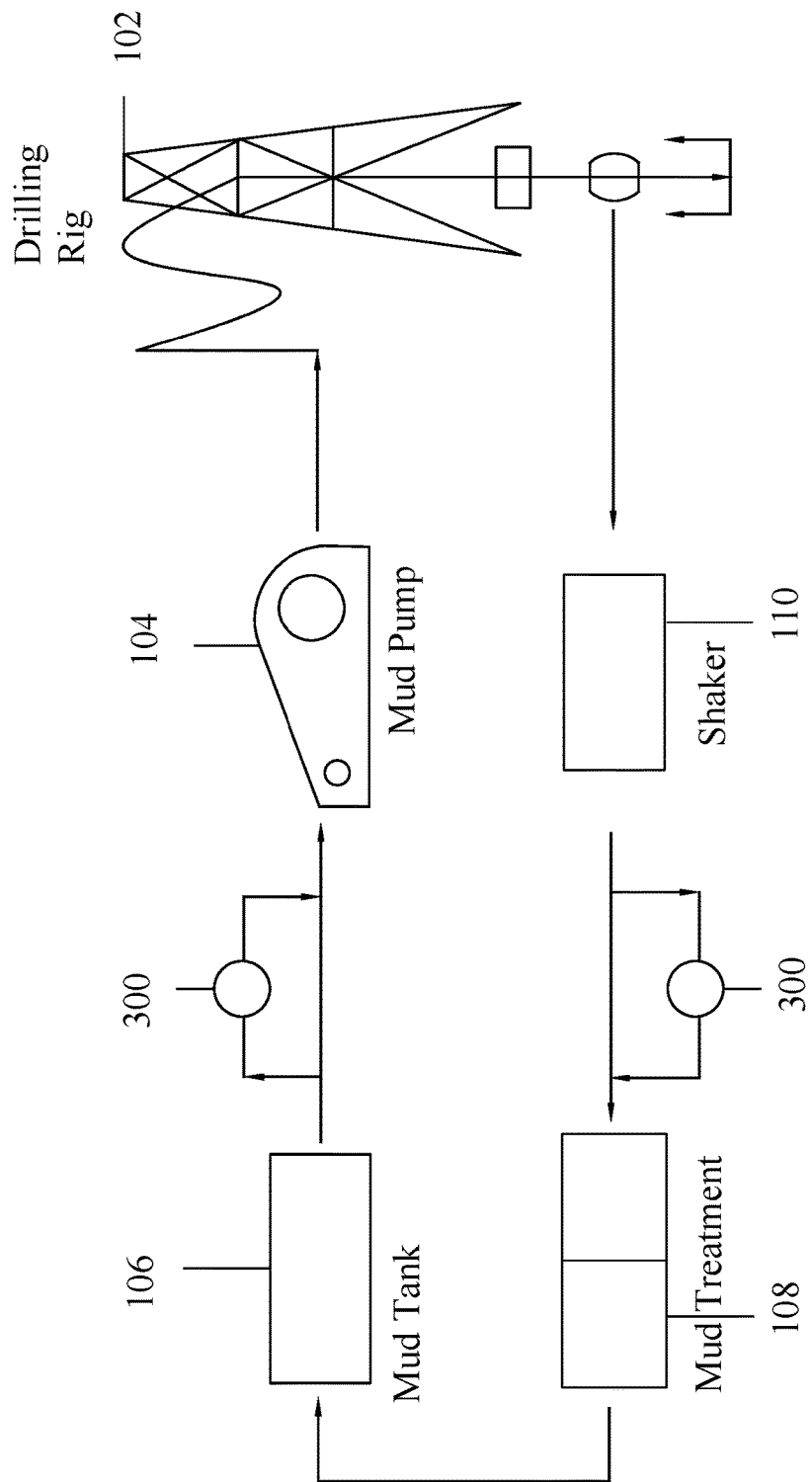
FIG. 1 is a schematic representation of the fast response fluid properties monitoring system at a drilling location.

| Reference Numerals in Drawings | |
|---|---|
| 102 | Drilling Rig |
| 104 | Mud Pump |
| 106 | Mud Tank |
| 108 | Mud Treatment |
| 110 | Shaker |
| 202 | Fracturing Truck |
| 204 | Fracturing Fluid |
| 206 | Well Head |
| 208 | Formation |
| 210 | Production Casting |
| 212 | Fracture |
| 214 | Production Zone |
| 300 | Fast Response Fluid Properties Monitoring System |

DETAILED DESCRIPTION

Embodiments disclosed herein relate generally to a system and method for measuring fluid properties at a drilling or fracturing location. More specifically, embodiments disclosed herein relate to systems and methods for fast evaluating and predicting properties of drilling fluid and fracturing fluid onsite of oilfield.

FIG. 1 shows a schematic representation of a fast response fluid properties monitoring system 300 at a drilling location. FIG. 1 consists of a drilling fluid that is pumped into a wellbore, through a drilling rig 102, a drilling string and a drill bit, to facilitate the drilling string, cool and lubricate the drill bit, and remove solid particles from the wellbore. Afterwards, the drilling fluid is transported through a shaker 110 and a mud treatment 108. Then the drilling fluid is then circulated back to a mud tank 106 then to a mud pump 104 and back to the drilling rig 102 where the operation started. A fast response fluid properties monitoring system 300 can be either installed after the shaker 110, before a mud pump 104, or in another place that is needed.

As the drilling fluid circulates through the wellbore, solid particles, including drill cuttings, become entrained within the drilling fluid and are conveyed from the wellbore to the surface of the drilling operation. Because characteristics of the drilling fluid may change as a result of the circulation of the fluid through the wellbore, those of ordinary skill in the art will appreciate that fast monitoring of the drilling fluid may be beneficial. Examples of fluid characteristics that may change include fluid density, viscosity, rheology, temperature, and pH, as well as other components of the drilling fluid. Also, as the drilling fluid circulates through the wellbore, the fluid removes entrained cuttings, and as such, characteristics of the drilling fluid may be affected by the addition of drill cuttings, hydrocarbons, and other contaminants. Therefore, it is important to measure the properties of the drilling fluid, fast evaluate and predict the properties, and make a quick adjustment according to the current drilling fluid characteristics. This is why the fast response fluid properties monitoring system 300 can be so vital to the industry today.

Figure 2:
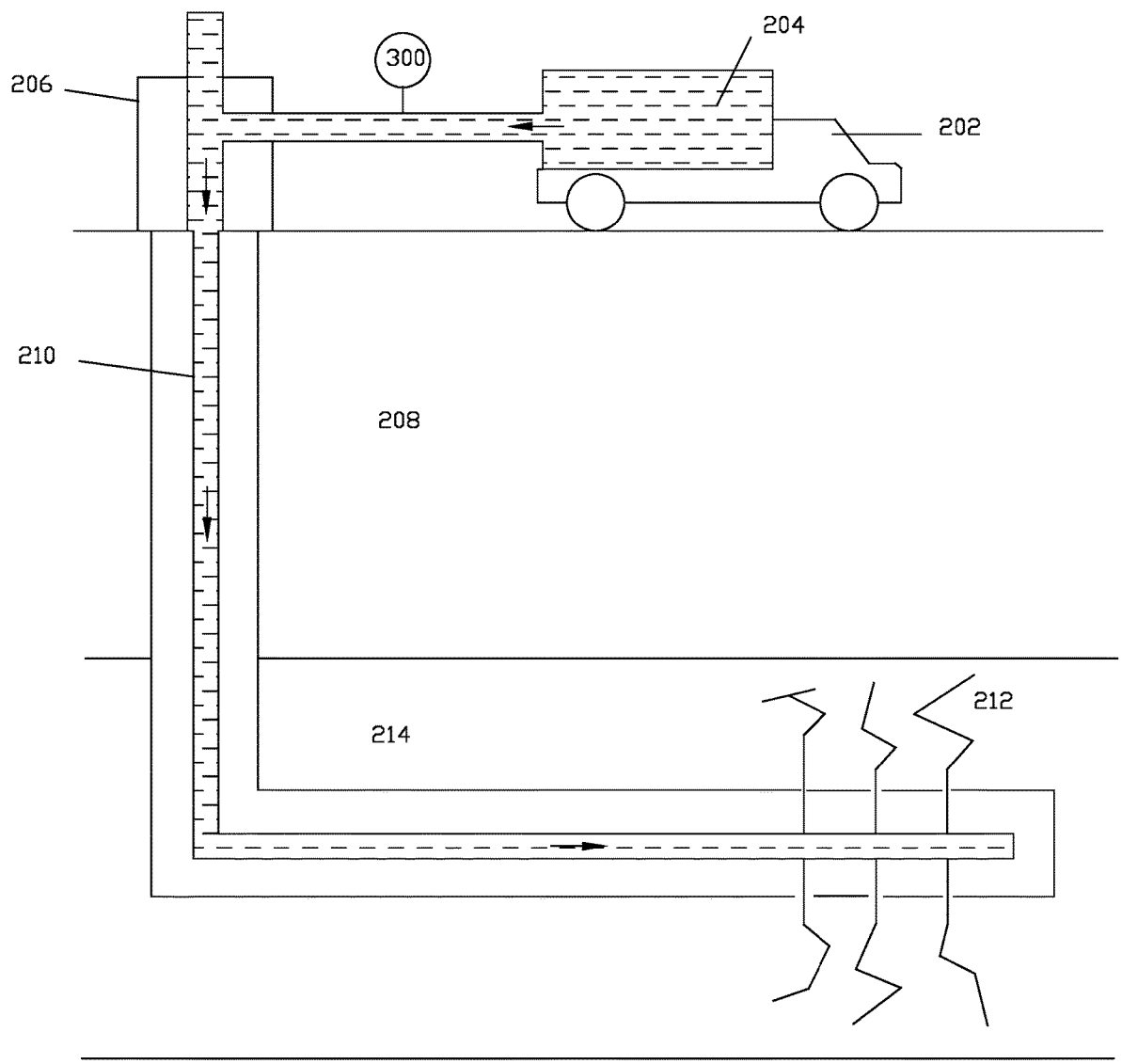
FIG. 2 is a schematic representation of the fast response fluid properties monitoring system at a fracturing location.

FIG. 2 shows a schematic representation of the fast response fluid properties monitoring system 300 at a fracturing location. FIG. 2 consists of a fracturing truck 202, which pumps a fracturing fluid 204 that leads into a formation 208 through a well head 206 and a production casing 210 in order to generate and maintain a fracture 212 when the hydraulic pressure is over formation pressure. The fracture fluid 204 contains proppant which is made of sand or ceramic for maintaining the fracture and to increase the permeability of a production zone 214. The viscosity of the fracturing fluid is related to the width of the fracture 212 and has the capability of transporting the propping agent into the fracture 212. The density of fracturing fluid 204 will affect the surface injection pressure and the ability of the fracturing fluid 204 to flow back after the treatment. The fast response fluid property monitoring system 300 can be installed on the pipe line of the fracturing fluid 204 in order to have a fast evaluation and prediction of the properties of fracturing fluid 204.

Figure 3:
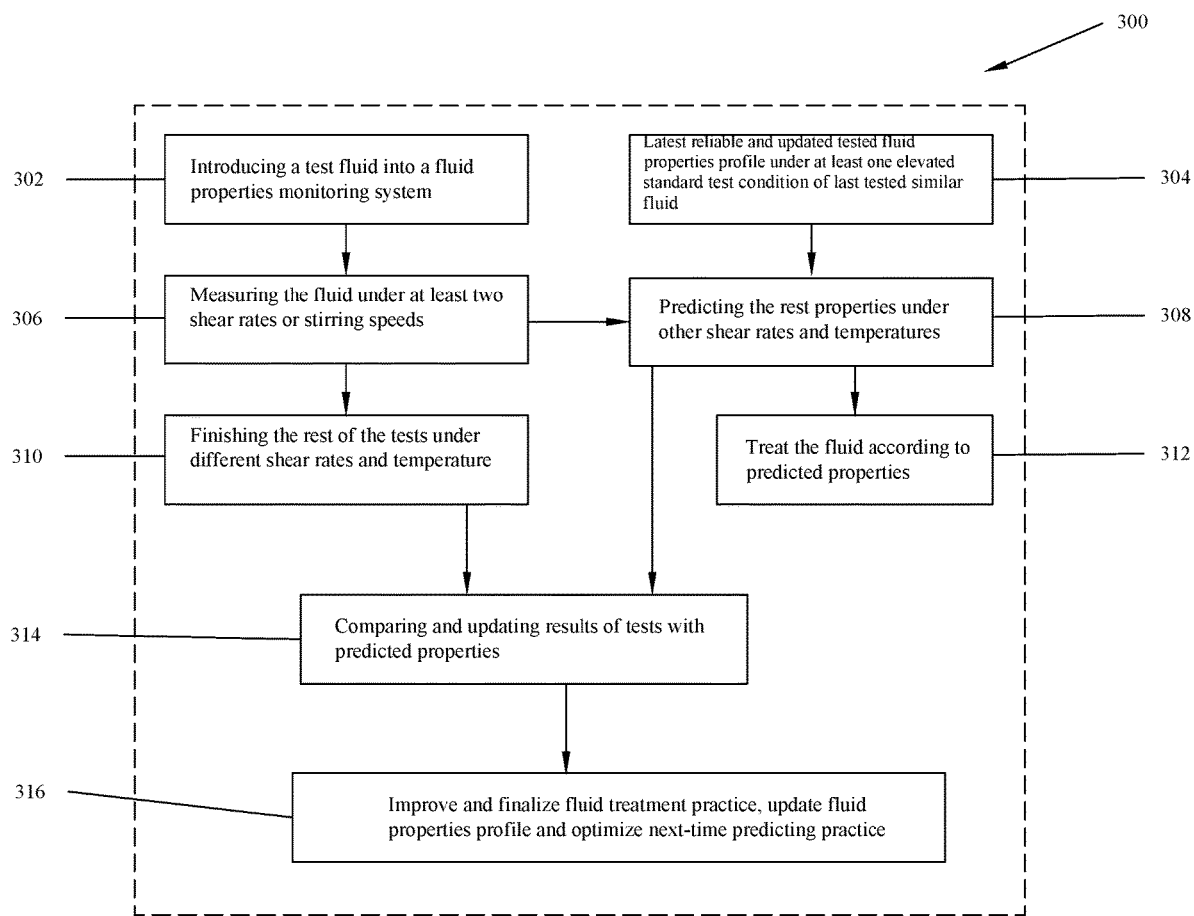
FIG. 3 is a flow chart of the fast response fluid properties monitoring system.

FIG. 3 shows a flow chart of the fast response fluid properties monitoring system 300. Generally, drilling fluid, fracturing fluid, or cement is measured or monitored by a field engineer who determines whether these fluids meet the drilling requirements before and during oilfield operation. The measurement of these properties gives the field engineer a status report of the fluid and how it is reacting with the formation and the subsurface environment. These fluids undergo constant proper treatment and adjustment so that the fluid properties, including density and rheology, are maintained to the best condition for current drilling operations. Drilling fluid is used to remove drill cuttings from the bottom of the hole among other things and the temperature is elevated so the drilling fluid properties experience numerous changes. Since drilling fluid properties experience changes corresponding to temperature changes, a typical drilling program, used to control drilling and mud treatment process, only requires a target rheology property of drilling fluids at 120° F. for a shallow well and 150° F. for a deep well. In this case, 120° F. or 150° F. is regarded as an elevated standard temperature testing condition. In this embodiment, a test fluid is introduced 302 into a fluid properties monitoring system 300. The fluid properties monitoring system 300 may include a viscometer, a densiometer or other devices used to measure fluid rheology or other similar properties. The test fluid will not be required to be heated to an elevated standard testing temperature in order to save time; therefore the rheology measurement will be conducted immediately at the current temperature under two different shear rates 306. The most commonly used shear rates are corresponding to 300 rpm and 600 rpm testing speeds when using an API 13 compliant rheometer.

Before the drilling process occurs, a set of measured rheology numbers should already be obtained through testing originally designed drilling fluid 304. While drilling, at least two shear stress readings under 600 rpm and 300 rpm can be measured at current temperature 306 for when the drilling fluid has returned to the top. These two shear stress measurements can be used to predict the properties at an elevated standard temperature using the mathematical method 308. In the preferred embodiment first obtain one or two quickly measured rheology numbers at current temperature. Then derive the properties of the tested fluid at current temperature based on latest tested data of last fluid which is similar to currently tested fluid at an elevated standard temperature condition. Once the current temperature properties are measured, the derived properties at the current temperature would then be compared to the measured properties at the current temperature. The difference between the measured and derived numbers would be used to predict the properties of fluids currently being measured at elevated standard conditions such as 120° F. and 150° F. The fluid is then treated according to this prediction 312. The mathematical method described is very similar to the practice of extrapolation and interpolation. Meanwhile, fluid that is currently being tested is heated to elevated standard temperature and its properties are measured thereafter 310. These measured properties are compared to the predicted properties at the elevated standard temperature 314. If there is not a difference between the measured and the derived properties, then the mathematical method does not require an improvement. If there is a difference between the predicted and measured properties, then the difference is used to improve the method of prediction of future drilling fluid properties 316.

An example of a mathematical method that can be used to predict or derive drilling fluid properties is the power law extrapolation. For example, the equation used to find the power law extrapolation for dial readings at 600 rpm at constant pressure is as follows, $$d_{600} = n_{600} * t^k \qquad \text{(Equation 1)}$$

where t is the temperature and $d_{600}$ is the dial reading at that particular temperature. The equation shown has two unknowns, $n_{600}$, and k, therefore one who is skilled in the art will be capable of using the two different known temperatures and corresponding dial readings at 600 rpm to solve for the unknowns. Linear extrapolation or any other form of mathematical method can be used as a prediction method to predict the dial readings at other shear rates as well. For example, if the data for the ten second and ten minute gel strength was predicted by using linear extrapolation, under constant pressure the following formula could be used, $$gs(t_*) = n_{gs} * t_* + b_{gs} \qquad \text{(Equation 2)}$$

where the unknown gel strength is $gs(t_*)$ at the temperature $t_*$ and $n_{gs}$ and $b_{gs}$ are the unknown constants.

In actuality a wellbore environment and a fracturing location have elevated temperatures as well as elevated pressure conditions. Some may choose to assume constant pressure to predict the properties at an elevated temperature as stated above and then make assumptions with the pressure. But in a more advanced treatment program the pressure as well as the temperature should be derived or predicted for the prediction of the drilling fluid properties as it travels down a wellbore or a formation. The mathematical method can also be utilized for constant temperature by using the following equation, $$d(p_*) = n_p * p_* + b_p \qquad \text{(Equation 3)}$$

Where $p_*$ is the pressure, $n_p$ and $b_p$ are constants, $d(p_*)$ is the dial reading for the corresponding pressure. Drilling fluid properties normally exhibit a linear pattern as the pressure increases, if temperature is constant. One who is skilled in the art will be capable of using the two different known pressures and corresponding dial readings at a single rpm to solve for the unknowns. If the rheological properties of the original mud are known at two different pressures, for example 2000 psi and 5000 psi, Equation 3 can be used to predict the rheological properties of the current mud at an elevated pressure. A combination of Equation 1 and Equation 3 can be used to predict or derive the rheological properties of the drilling fluid at elevated temperatures and elevated pressures by using a mathematical method that would help to find the current drilling fluid properties at the current temperature and pressure. Once the derived data is found, it will be compared to the measured data at the current temperature and pressure. If there are any differences between the derived properties and the current drilling fluid properties these differences will be applied to the prediction of the elevated standard temperature and pressure, for example 120° F. at 5000 psi and the fluid will be treated according to this prediction 312. In this way the results will be updated and will be optimized for next-time predicting practice 316. The described mathematical methods are not limited to predicting or deriving dial readings or gel strengths, these methods can also be used to derive and predict other fluid properties such as density, and other desirable properties of the drilling fluid.

EXAMPLES

The following examples are displayed in order to facilitate a better understanding of the described embodiment of the present disclosure. In no way should the following examples be read to limit, or to define, the scope of the present disclosure.

Example 1

Figure 4:
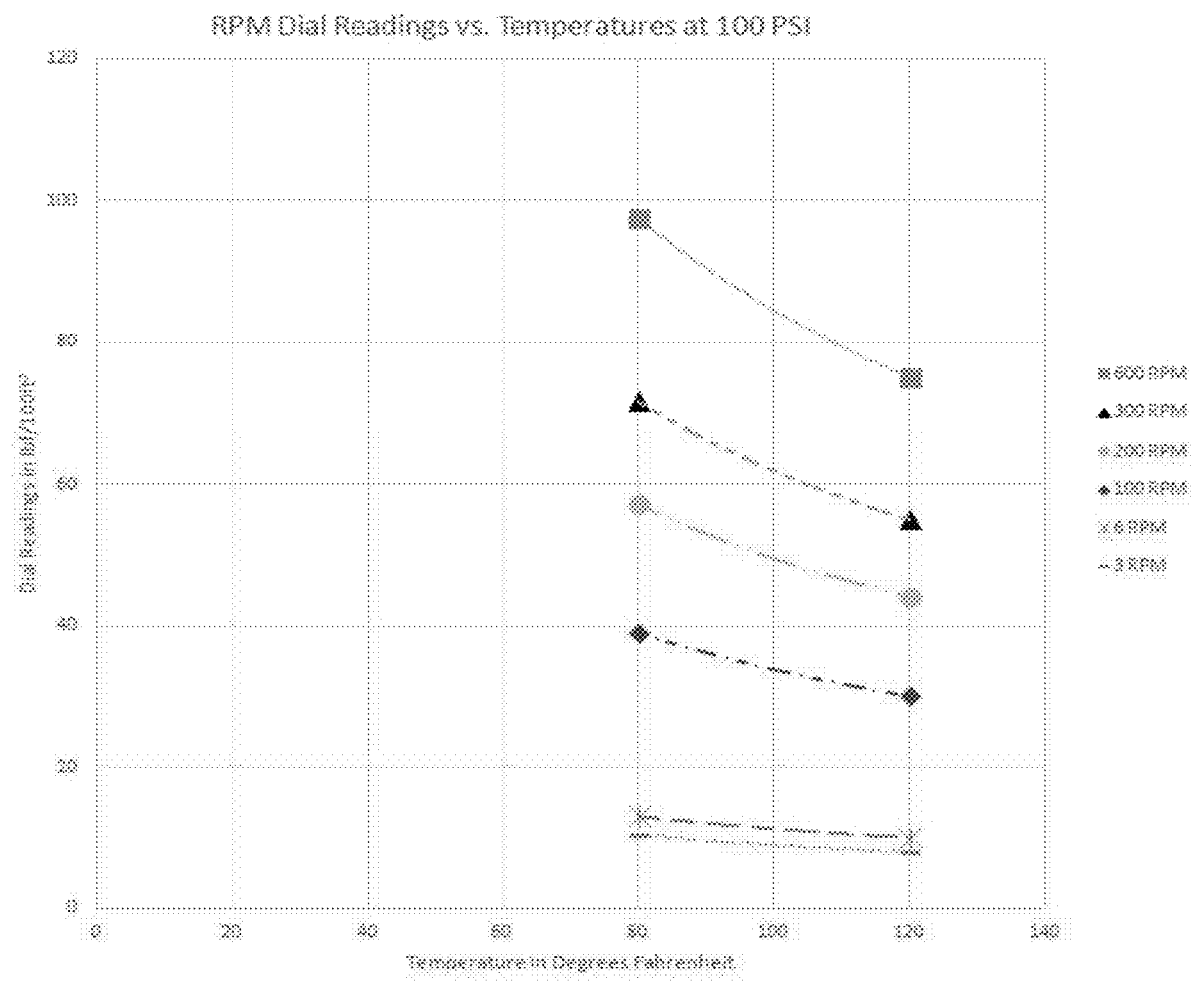
FIG. 4 is a diagram of RPM dial readings vs. temperatures at 100 psi.

The original mud properties for 80° F. and 120° F., as shown in Table 1, are known before the drilling fluid or mud enters the monitoring system 300 at constant pressure, then the drilling fluid properties of the current mud at the current temperature, or 100° F. can be derived using the mathematical method from equation 1. The diagram of RPM dial readings vs. temperatures at 100 psi is shown in FIG. 4.

Figure 5:
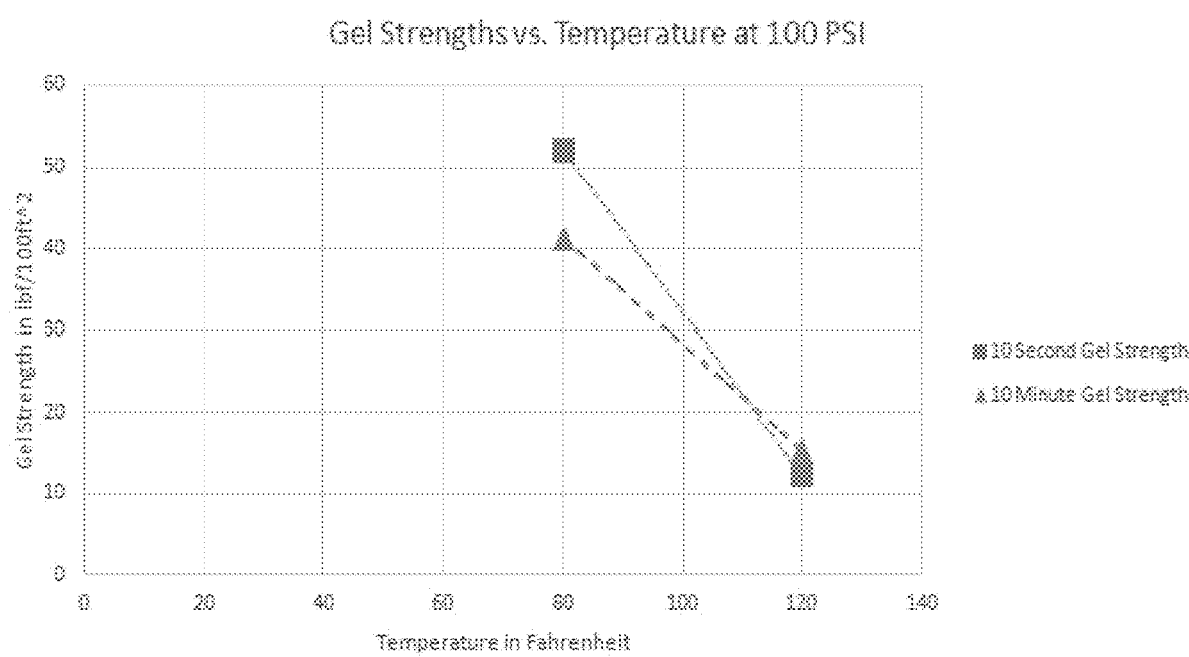
FIG. 5 is a diagram of 10-second and 10-minutes gel strength vs. temperature at 100 psi.

If the ten minute gel strength and the ten second gel strength are known at two different temperatures under constant pressure, the mathematical method shown in equation 2 can be used to find the ten second and ten minute gel strengths at different temperatures. In a similar manner, once the gel strengths are measured they can be compared to the predicted gel strengths, as displayed in Table 3, and if there is any difference between the two sets of data, this can be used as an improvement of the mathematical method for future predictions of the drilling fluid rheology properties. The diagram of 10-second and 10-minute gel strength vs. temperature at 100 psi is shown in FIG. 5.

TABLE 1

Measured Drilling fluid Data at 80° F. and 120° F.

| TEMP (° F.) | PRESS (PSI) | Dial Reading (lbf/100 ft²) at 3 RPM | Dial Reading (lbf/100 ft²) at 6 RPM | Dial Reading (lbf/100 ft²) at 100 RPM | Dial Reading (lbf/100 ft²) at 200 RPM | Dial Reading (lbf/100 ft²) at 300 RPM | Dial Reading (lbf/100 ft²) at 600 RPM | 10 sec Gel Strength (lbf/100 ft²) | 10 min Gel Strength (lbf/100 ft²) |
|---|---|---|---|---|---|---|---|---|---|
| 80 | 100 | 10.4 | 13 | 39 | 57.2 | 71.5 | 97.5 | 127.4 | 118.3 |
| 120 | 100 | 8 | 10 | 30 | 44 | 55 | 75 | 87.4 | 92.3 |

Assuming the drilling fluid was sampled to the viscometer at the current temperature of 100° F., then the properties at 100° F. are measured. These measured properties are compared to the derived properties at 100° F. under constant pressure. The results are shown in table 2. The differences between the measured and derived properties are used as an adjustment along with the mathematical method to predict fluid properties at elevated standard temperatures, in this case, 120° F.

TABLE 2

Measured and Derived Drilling Fluid Dial Readings at 100° F.

| Temp 100° F. Press 100 psi | Dial Reading (lbf/100 ft²) at 300 rpm | Dial Reading (lbf/100 ft²) at 600 rpm |
|---|---|---|
| Measured | 61.9 | 84.4 |
| Derived | 63 | 85.5 |

As stated above the difference between the measured data at 100° F. and the derived data at 100° F. was noted and used along with the mathematical method in order to predict the data at 120° F. While the data at the elevated standard temperature, or 120° F. is being measured the fluid is being treated based on the predicted properties at that temperature. Once the measurement at 120° F. is completed, it's result is compared to the predicted data at 120° F. as shown in Table 3. The drilling program will use this updated measurement to update its fluid treatments. Furthermore, the difference in data is used to improve the prediction method of fluid properties at next sample testing.

Figure 6:
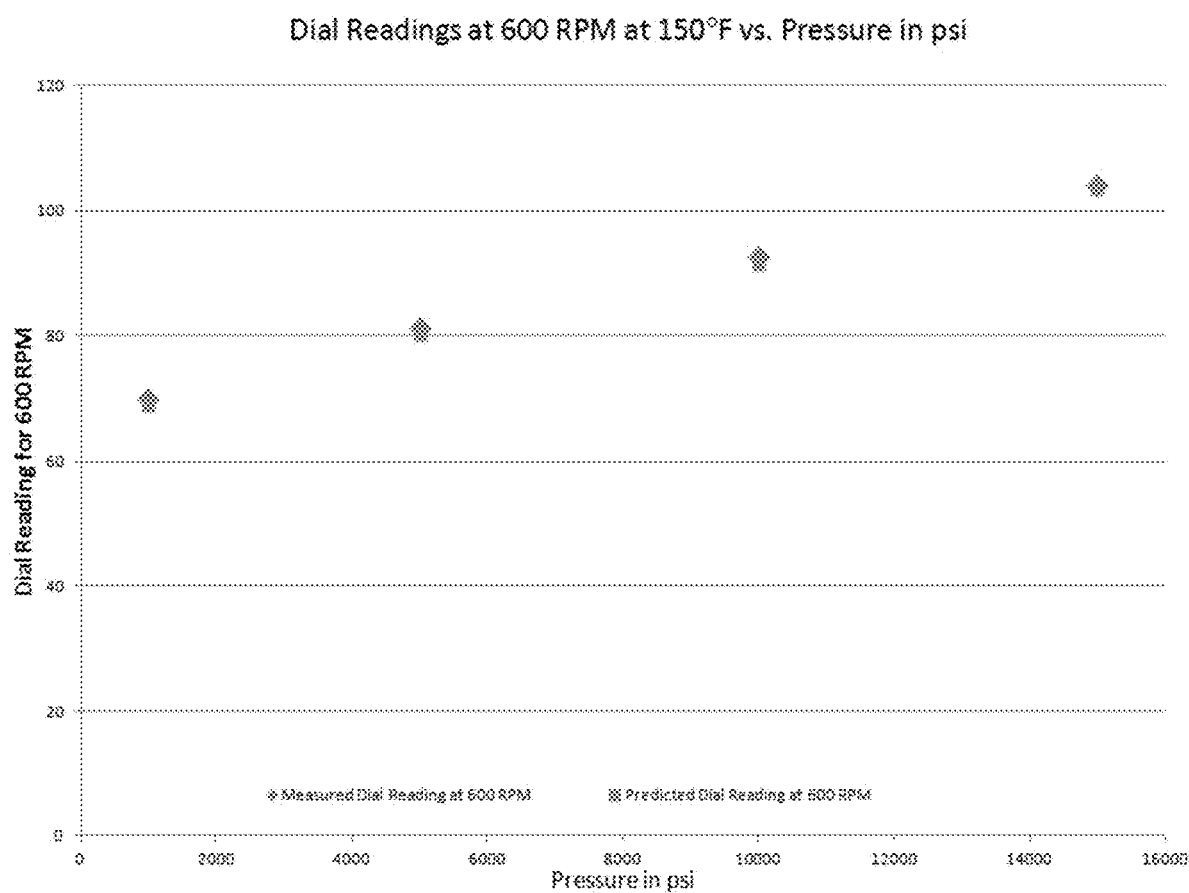
FIG. 6 is a diagram of predicted and measured dial readings at 600 RPM at 150° F. vs. pressure in psi.

If the rheological properties of the original drilling fluid are known at two different pressures, for example 1000 psi and 5000 psi, and at two different temperatures (as shown in table 4) then equation 1 and equation 3 can be used to predict the rheological properties of the current mud at an elevated pressure and elevated temperature. Once the properties are measured at these pressures and temperatures, the predicted properties are then compared to the measured properties, as shown in Table 5. If there is little to no difference between the measured and predicted properties, then the mathematical method does not require an improvement. If there is a difference between the measured properties and the predicted properties then the difference is used as an improvement of the mathematical method for future predictions of the drilling fluid rheology properties. The diagram of predicted and measured dial readings at 600 RPM at 150° F. vs. pressure in psi is shown in FIG. 6.

TABLE 4

Known dial readings at 600 RPM

| Dial Reading at 600 RPM | Temperature (° F.) | |
|---|---|---|
| Pressure (psi) | 80 | 120 |
| 1000 | 108.9 | 74.8 |
| 5000 | 120.2 | 86.1 |

TABLE 3

Measured and Predicted Drilling fluid Data at 120° F.

| Temp 120° F. Press 100 psi | Dial Reading (lbf/100 ft²) at 3 RPM | Dial Reading (lbf/100 ft²) at 6 RPM | Dial Reading (lbf/100 ft²) at 100 RPM | Dial Reading (lbf/100 ft²) at 200 RPM | Dial Reading (lbf/100 ft²) at 300 RPM | Dial Reading (lbf/100 ft²) at 600 RPM | 10 s gel (lbf/100 ft²) | 10 min gel (lbf/100 ft²) |
|---|---|---|---|---|---|---|---|---|
| Measured | 8 | 10 | 30 | 44 | 55 | 75 | 12.3 | 15.4 |
| Predicted | 8.3 | 10.1 | 30.3 | 44.2 | 55.3 | 75.4 | 12.6 | 15.9 |

TABLE 5

Measured and Predicted Dial Readings using
Extrapolation Mathematical Methods for 600 RPM

| Pressure (psi) | Temp (° F.) | Measured Dial Reading at 600 RPM | Predicted Dial Reading at 600 RPM |
|---|---|---|---|
| 1000 | 150 | 69.9 | 68.8 |
| 5000 | 150 | 81.3 | 80.2 |
| 10000 | 150 | 92.6 | 91.5 |
| 15000 | 150 | 104 | 103.5 |

Ramifications

In FIG. 1, the fast response fluid properties monitoring system 300 can be placed after the shaker 110, after the mud tank 106, or other places that are needed.

In FIG. 1, any type of drilling fluid may be used, if it can be safely used and contained in the fast response fluid properties monitoring system 300 at a drilling location In FIG. 2, any type of vehicle or fracturing device may be used if it can pump a fracturing fluid 204 through a well head 206 and a production casing 210 to generate and maintain a fracture 212.

In FIG. 2, any type of fracturing fluid 204 may be used, if it can be safely used and contained in the fast response fluid properties monitoring system 300 at a fracturing location In FIG. 3, after measuring the fluid under at least two shear rates or stirring speeds 306, the rest properties are predicted under other shear rates and temperatures 308 and the rest of the tests are finished under different shear rates and temperatures.

In FIG. 3, after predicting the rest properties under other shear rates and temperatures 308, the fluid is treated according to the predicted properties 312 and the measured fluid properties results are compared and updated with the predicted properties 314 and eventually help to update fluid properties profile and optimized next time predicting practice 316.

In FIG. 3, the fluid properties monitoring system 300 may include a electrical stability meter, a resistivity meter, or any other devices that is used to measure fluid properties.

In FIG. 3, any type of fracturing fluid 204, drilling fluid or otherwise may be used, if it can be safely used and contained in the fast response fluid properties monitoring system 300.

In FIG. 3, any type of mathematical method may be used, if it accurately predicts the fluid properties and or the density of the drilling fluid.

In FIG. 3, any type of mathematical method may be used, if it accurately predicts the fluid properties and or the density of the fracturing fluid.

CONCLUSION AND SCOPE

Accordingly, the reader skilled in the art will see that this invention and method can be used to quickly determine and monitor fluid properties on site of an oilfield operation. In doing so it satisfies an eminent need for the oil industry which requires fluid properties of a drilling fluid to quickly be monitored and adjusted as it goes through a drilling location and fracturing location. Accordingly, the scope of the fast response fluid properties monitoring system 300 should be determined not by the embodiments illustrated, but by the appended claims and their legal equivalents.

The invention claimed is:

1. A fast response fluid properties monitoring system comprising:
   a) a viscometer to measure viscosity properties of a sample fluid,
   b) a temperature control device to manipulate temperature of said sample fluid to at least an elevated standard temperature condition,
   c) a mud treatment system capable of treating said sample fluid according to the input of said viscosity properties of said sample fluid under at least said elevated standard temperature condition,
   d) a mathematical procedure to predict viscosity properties of said sample fluid based on a quickly measured rheology properties of said sample fluid at current temperature under at least one shear rate and previously measured viscosity properties of a second similar sample fluid under said elevated standard temperature condition.

2. The system of claim 1, wherein said sample fluid is a drilling mud.

3. The system of claim 1, wherein said viscometer is capable of measuring fluid properties of said sample fluid at various pressures.

4. The system of claim 1, wherein viscosity properties comprise, but are not limited to, viscosity, ten second gel strength, and ten minute gel strength.

5. The system of claim 1, wherein said predicted viscosity properties are further compared to said sample fluid measured fluid properties under at said elevated standard temperature to optimize said mathematical procedure to predict viscosity properties of said sample fluid.

6. The system of claim 1, wherein said mud treatment system is at a drilling location.

7. A method for a fast response fluid properties monitoring system, comprising the steps of:
   a) obtaining fluid properties of a first sample fluid through testing under at least an elevated standard temperature condition,
   b) obtaining minimum required properties of a second sample fluid which is similar to said first sample fluid at a current temperature conditions,
   c) predicting said second sample fluid properties at said elevated standard temperature condition according to the fluid properties of said first sample fluid under at least said elevated standard temperature condition and said minimum required properties of said second sample fluid,
   d) treating said second sample fluid based on said predicted fluid properties of said second sample fluid at said elevated standard temperature condition,
   e) finishing testing of said second sample fluid at said elevated standard test condition to improve said predicting accuracy of said second sample fluid properties for the future.

8. The method of claim 7, wherein said fluid properties comprise, but are not limited to, viscosity, ten second gel strength, ten minute gel strength, and density.

9. The method of claim 7, wherein said first sample fluid and said second fluid comprises, but is not limited to, at least one of a group consisting of a drilling fluid and fracturing fluid.

10. The method of claim 7, wherein said first sample fluid and said second sample fluid properties at a set of temperature and pressure conditions is measured using a viscometer.

11. The method of claim 7, wherein said first sample fluid and said second sample fluid properties at a set of temperature and pressure conditions is measured using a densitometer.

12. The method of claim 7, wherein said obtaining fluid properties of a first sample fluid through testing under at least an elevated standard temperature condition further comprises obtaining fluid properties of a first sample fluid through testing under at least an elevated pressure condition.

13. The method of claim 12, wherein said predicting said second sample fluid properties at said elevated standard temperature condition according to the fluid properties of said first sample fluid under at least said elevated standard temperature condition and said minimum required properties of said second sample fluid, further comprising predicting said second sample fluid properties at said elevated standard temperature condition and said at least an elevated pressure condition according to the fluid properties of said first sample fluid under at least said elevated standard temperature condition and said at least an elevated pressure condition and said minimum required properties of said second sample fluid.

\* \* \* \* \*